US00PP30578P2

(12) United States Plant Patent
Lewers et al.

(10) Patent No.: US PP30,578 P2
(45) Date of Patent: Jun. 18, 2019

(54) STRAWBERRY PLANT NAMED 'KEEPSAKE'

(50) Latin Name: ***Fragaria* x *ananassa* Duchesne ex Rozier**
Varietal Denomination: Keepsake

(71) Applicant: The United States of America, as Represented by the Secretary of Agriculture, Washington, DC (US)

(72) Inventors: Kimberly S. Lewers, Columbia, MD (US); John M. Enns, Hyattsville, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/998,140

(22) Filed: Jul. 9, 2018

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208
See application file for complete search history.

*Primary Examiner* — Annette H Para
(74) *Attorney, Agent, or Firm* — John Fado; Ariel Atkinson

(57) ABSTRACT

This invention relates to a new and distinct cultivar of strawberry named 'Keepsake'. The new cultivar is primarily characterized by the superior shelf life of the fruit and by the sweetness of the fruit.

7 Drawing Sheets

Latin name of the genus and species of the plant claimed: 'Keepsake' is a new strawberry plant that is *Fragaria* x *ananassa* Duchesne ex Rozier.

Variety denomination: The new strawberry plant claimed is of the variety denominated 'Keepsake' *Fragaria* x *ananassa* Duchesne ex Rozier.

BACKGROUND OF THE NEW PLANT

The present invention relates to a new and distinct strawberry cultivar designated 'Keepsake' and botanically known as *Fragaria* x *ananassa* Duchesne ex Rozier. This new strawberry cultivar was discovered in Beltsville, Md., in Spring 2007 and originated from a cross between the female parent B1031 (unpatented) and the male parent B1181 (unpatented). The original seedling of the new cultivar was asexually propagated in Beltsville since 2007 by rooting daughter plants from stolons of a mother plant. The present invention has been found to be stable and reproduce true to type through successive asexual propagations rooting daughter plants from stolons.

BRIEF DESCRIPTION OF THE PHOTOGRAPHS

This new strawberry plant is illustrated by the accompanying photographs that show the flowers, fruit and entire plants; the colors shown are as true as can be reasonably obtained by conventional photographic procedures.

DETAILED DESCRIPTION OF THE NEW CULTIVAR

Figure 1:
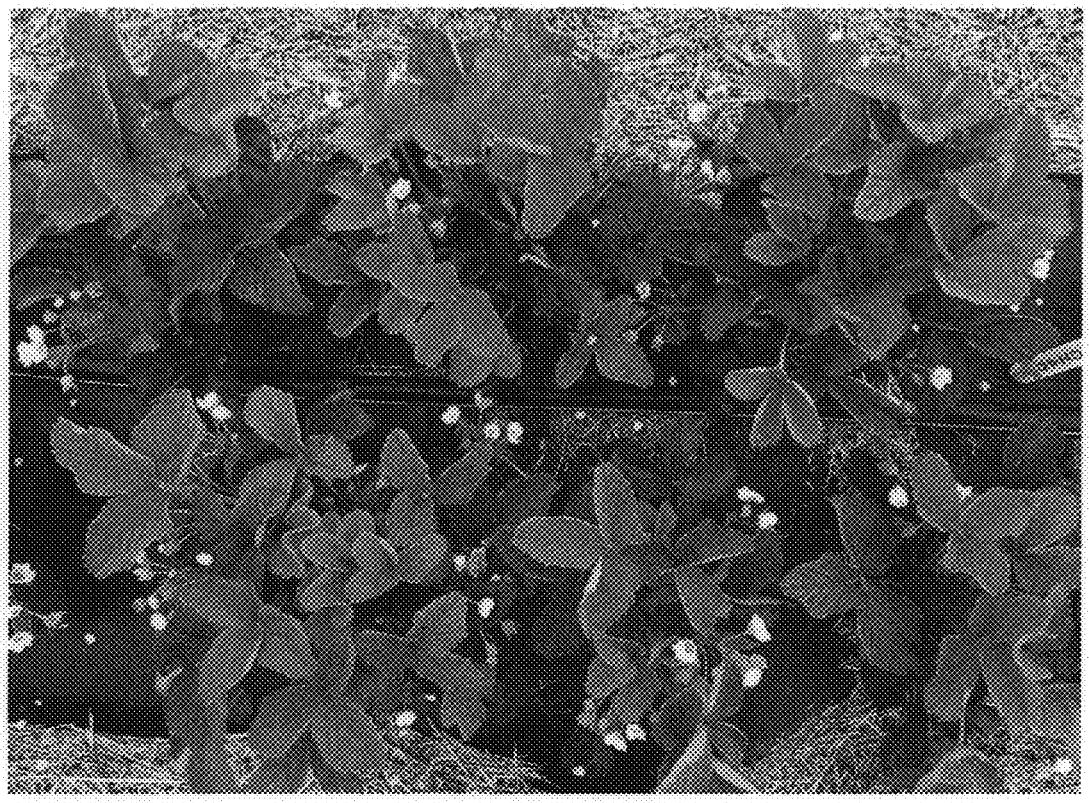
FIG. 1 shows shows 'Keepsake' plants, with 30.5 cm spacing, in annual plasticulture.
Figure 2:
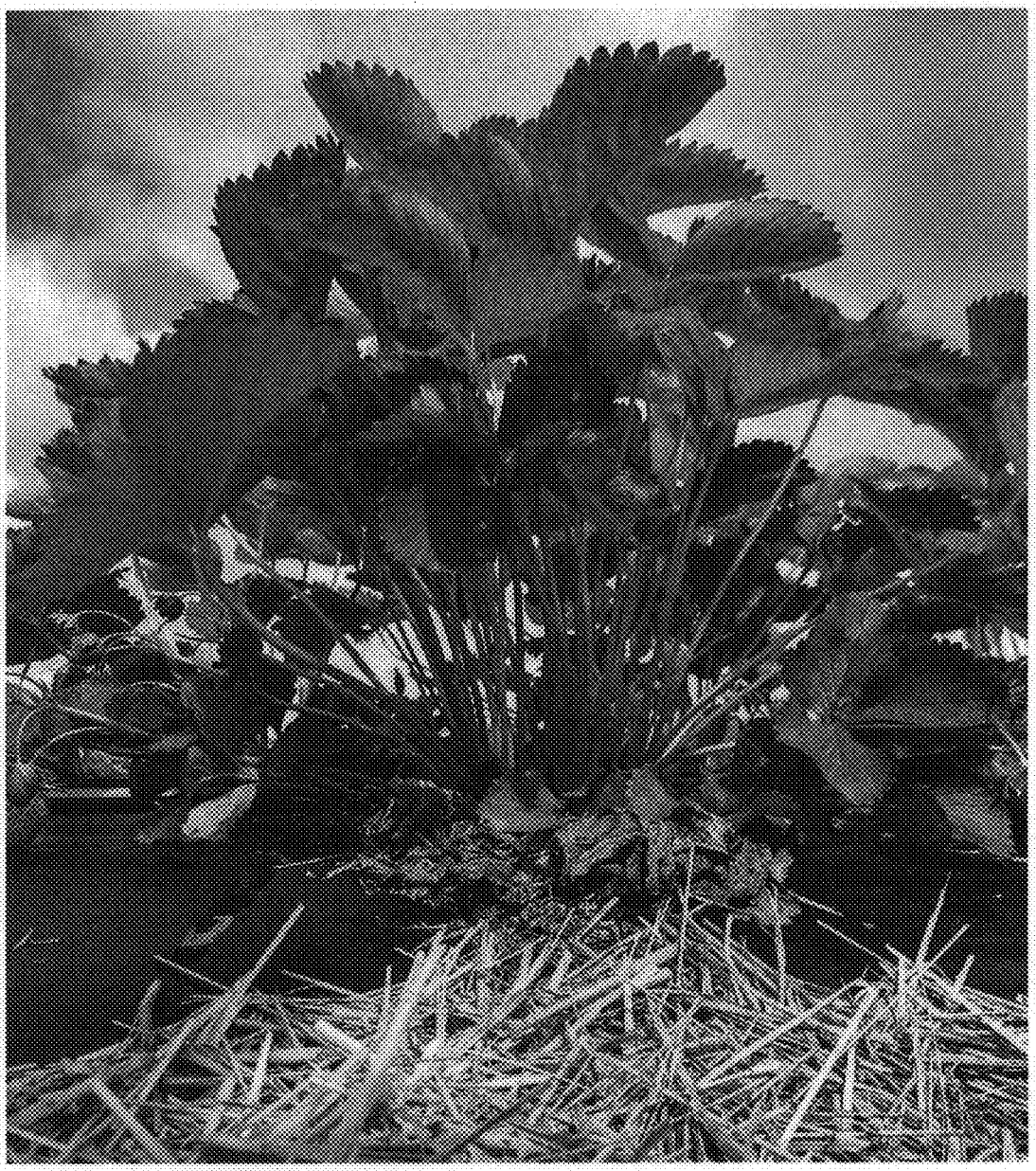
FIG. 2 shows a single 'Keepsake' plant.
Figure 3:
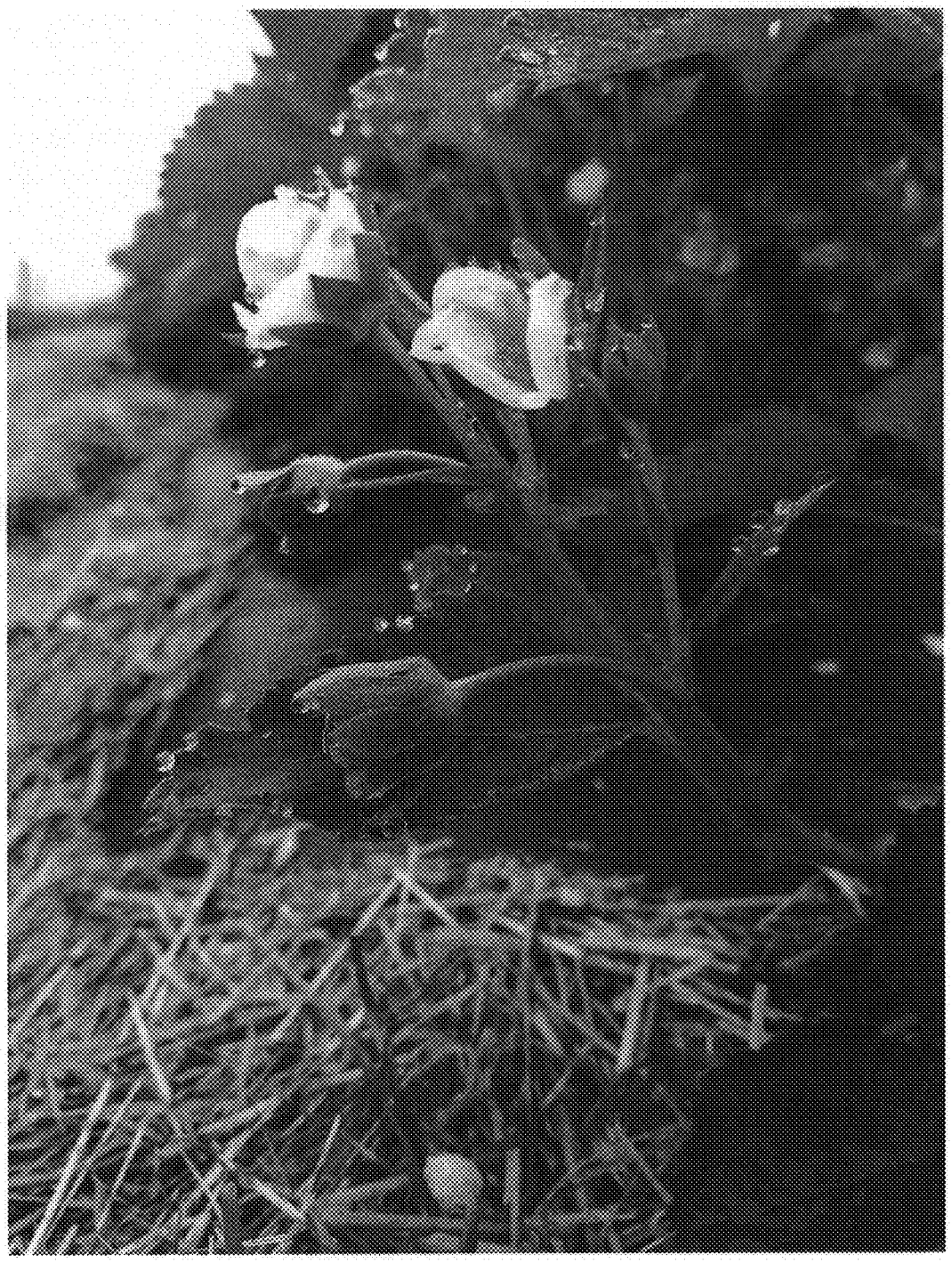
FIG. 3 shows a single 'Keepsake' flowering truss.
Figure 4:
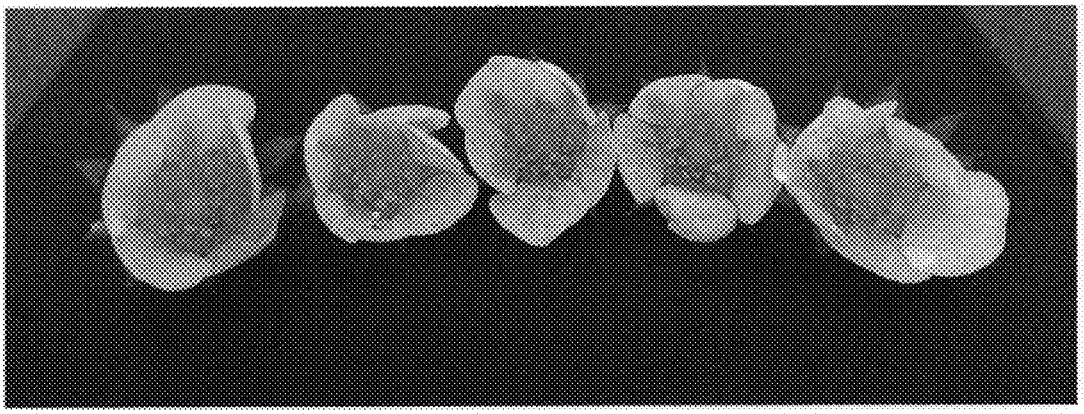
FIG. 4 shows typical 'Keepsake' detached flowers.
Figure 5:
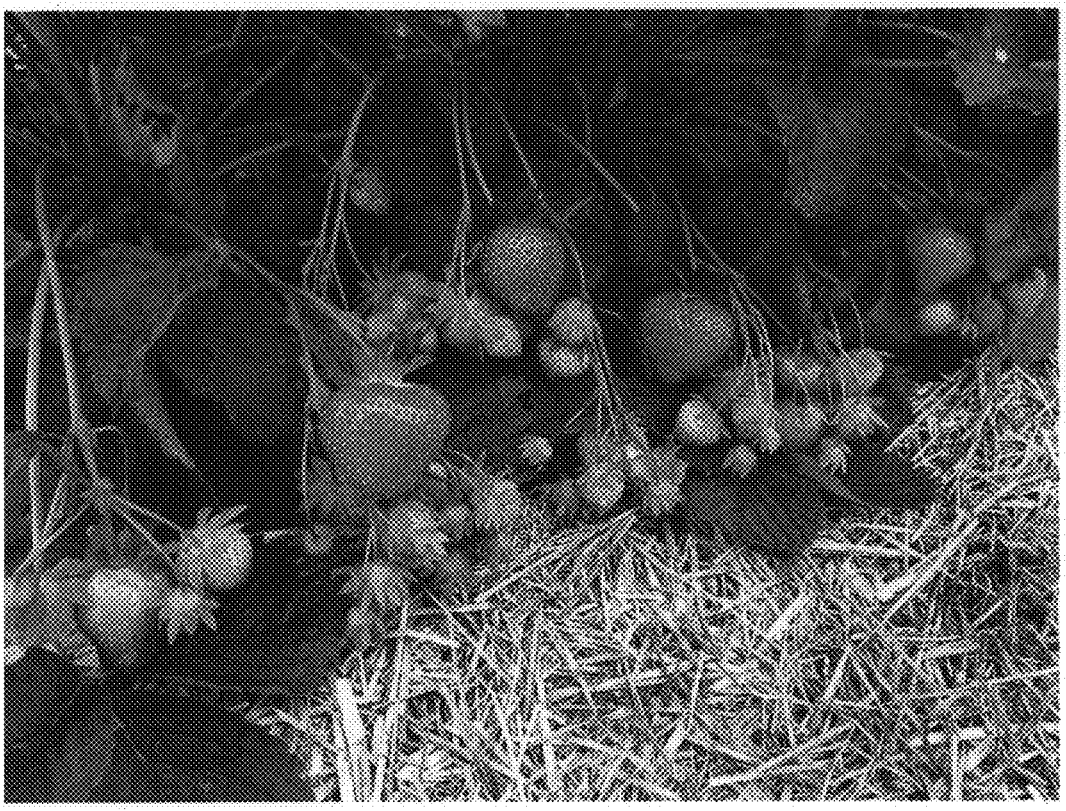
FIG. 5 shows typical 'Keepsake' fruit at various ripening stages.
Figure 6:
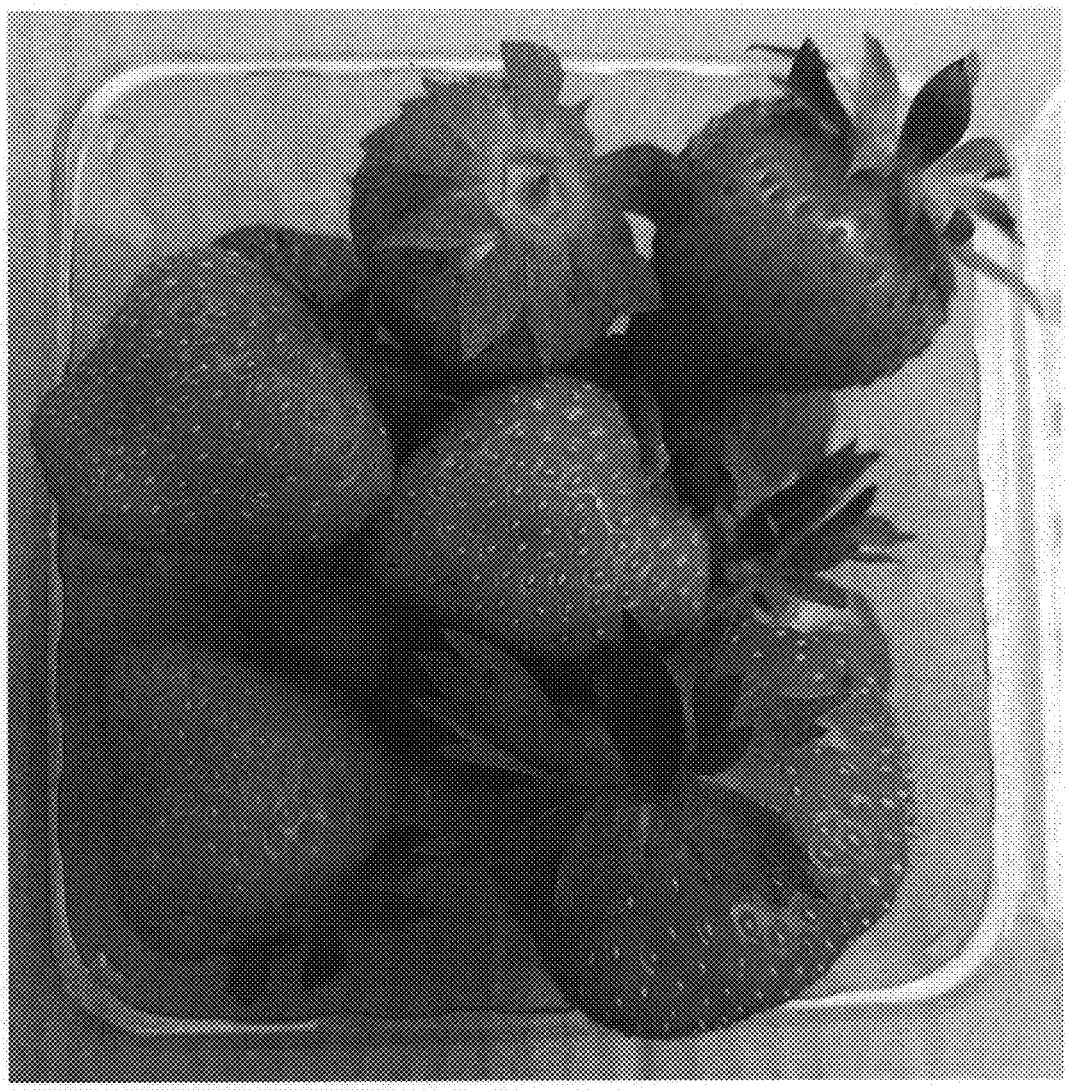
FIG. 6 shows a container of 'Keepsake' fruit.
Figure 7:
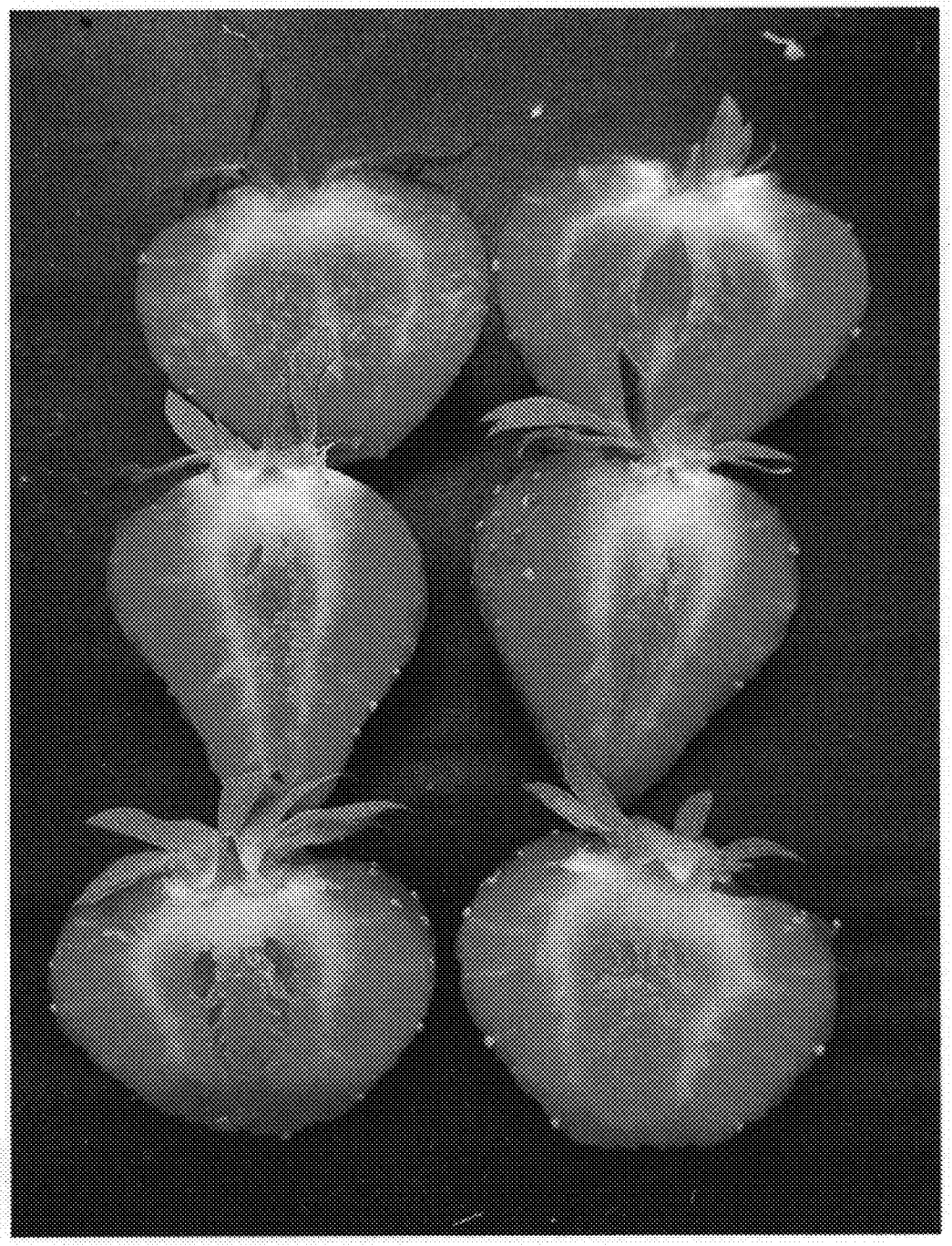
FIG. 7 shows typical halved 'Keepsake' fruits.

The following description of 'Keepsake' is based on observations taken from the 2008 through 2018 growing seasons in evaluations in Beltsville, Md. This description is in accordance with UPOV terminology. Color designations, color descriptions, and other phenotypical descriptions may deviate from the stated values and descriptions, depending on variation in environmental, seasonal, climatic, and cultural conditions. 'Keepsake' has not been observed under all possible environmental conditions. The botanical description of 'Keepsake' was taken from plants nine months after establishment in the field. Color terminology follows The Royal Horticultural Society Colour chart, London (RHS86).

DETAILED BOTANICAL DESCRIPTION

Table 1 shows selected characteristics of the new cultivar compared with plant characteristics of 'Flavorfest', the closest comparable commercial cultivar. Characteristics include density of individual plant, anther count, pose of calyx segments, size of calyx in relation to fruit, difference in shape between primaries and secondaries, and sweetness.

TABLE 1

| Characteristic | 'Keepsake' | 'Flavorfest' |
|---|---|---|
| Density of individual plant | Medium | Medium to dense |
| Anther count | 19.2 | 24.6 |
| Pose of calyx segments | Reflexed to spreading | Spreading to clasping |

TABLE 1-continued

| Characteristic | 'Keepsake' | 'Flavorfest' |
|---|---|---|
| Size of calyx in relation to fruit | Larger | Slightly smaller |
| Difference in shape between primary and secondary fruits | Moderate | Significant; depressed oblate primary fruits |
| Sweetness of fruit | Very sweet | Sweet |

Table 2 shows plant characteristics of the new cultivar compared with plant characteristics of 'Flavorfest'. Plant characteristics include plant height, diameter, number of crowns per plant, habit, and vigor.

TABLE 2

| Characteristic | 'Keepsake' | 'Flavorfest' |
|---|---|---|
| Plant height (cm) | 39.1 | 41.7 |
| Plant diameter (cm) | 45.7 | 61.5 |
| Number of crowns plant | 4.6, 4 to 5 | 4.6, 3 to 6 |
| Habit | Upright open globose | Upright open globose |
| Vigor | Medium to strong | Strong |

Table 3 shows leaf characteristics of the new cultivar compared with leaf characteristics of 'Flavorfest'. Leaf characteristics include leaf type, leaf shape. leaf length, leaf width, terminal leaflet length, terminal leaflet width, terminal leaflet length to width ratio, leaf margins, shape of teeth, leaf serrations per leaflet, upper and lower leaf surface color, number of leaflets, terminal leaflet apex shape, terminal leaflet base shape, glossiness upper side leaf surface, texture upper side leaf surface, texture underside leaf surface and leaf arrangement.

TABLE 3

| Characteristic | 'Keepsake' | 'Flavorfest' |
|---|---|---|
| Leaf type | Semi-evergreen | Semi-evergreen |
| Leaf shape | Trifoliolate with ovate leaflets touching to overlapping | Trifoliolate with ovate leaflets overlapping |
| Leaf length (cm) | 12.7 | 14.3 |
| Leaf width (cm) | 15.6 | 17.6 |
| Terminal leaflet length (cm) | 10.2 | 10.5 |
| Terminal leaflet width (cm) | 8.6 | 8.9 |
| Terminal leaflet length width ratio | 1.2 | 1.2 |
| Leaf margins | Serrate | Serrate |
| Shape of teeth | Apiculate | Apiculate |
| Leaf serrations per leaflet | 27.2 | 24.6 |
| Color mature leaves lower surface | Green Group 137C | Green Group 137C |
| Color mature leaves upper surface | Green Group 137A | Green Group 137A |
| Number of leaflets | 3 | 3 to 4, mostly 3 |
| Terminal leaflet apex shape | Obtuse | Obtuse |
| Terminal leaflet base shape | Acute cuneate | Acute cuneate |
| Glossiness upper side leaf surface | Semi-gloss | Semi-gloss |
| Texture upper side leaf surface | Very slightly rugose | Very slightly rugose |
| Texture underside leaf surface | Very slightly reticulate | Very slightly reticulate |
| Leaf arrangement | Individual trifoliate leaves attached to compressed stem (crown) a ground level | Individual trifoliate leaves attached to compressed stem (crown) at ground level |

Table 4 shows information about the petiole, the petiolule, the bract and the stipule of the new cultivar compared to 'Flavorfest'. This includes petiole length, petiole diameter, petiole pubescence, petiole color, petiolule color, petiolule length, bract frequency, texture petiole, stipule length, and stipule width.

TABLE 4

| Characteristic | 'Keepsake' | 'Flavorfest' |
|---|---|---|
| Leaf petiole length (cm) | 27.3 | 31.9 |
| Petiole diameter (cm) | 0.5 | 0.5 |
| Petiole pubescence | Very sparse | Sparse |
| Petiole color | Yellow Green Group 144B | Yellow Green Group 144A |
| Petiolule color | Yellow Green Group 144B | Yellow Green Group 144A |
| Petiolule length (cm) | 0.8 | 0.6 |
| Bract frequency | 1 to 2 per florescence, generally unifoliate | 1 to 2 per florescence, unifoliate and trifoliate |
| Texture petiole | Smooth | Smooth |
| Stipule length (cm) | 2.0 | 1.9 |
| Stipule width (cm) | 0.6 | 0.6 |

Table 5 shows stolon characteristics of the new cultivar compared to 'Flavorfest'. These characteristics include the number of stolons, the anthocyanin coloration of the stolons, the thickness of the stolons, and the pubescence of the stolons.

TABLE 5

| Characteristic | 'Keepsake' | 'Flavorfest' |
|---|---|---|
| Stolon production | 10 | 8 |
| Stolon anthocyanin | Medium | Medium |
| Stolon thickness (cm) | 0.3 | 0.3 |
| Stolon pubescence | Sparse | Sparse |

Table 6 shows inflorescence characteristics of the new cultivar compared to 'Flavorfest'. These characteristics include inflorescence position relative to foliage, flower type, flower size, petal shape, relative petal spacing, petal apex shape, petal margin, petal base shape, petal length, petal width, petal length/width ratio, number of petals, petal color, stigma color, style color, anther color, filament color, and flower truss type.

TABLE 6

| Characteristic | 'Keepsake' | 'Flavorfest' |
|---|---|---|
| Inflorescence position | Slightly below canopy | Slightly below canopy |
| Flower type | Complete simple | Complete simple |
| Flower diameter (cm) | 2.14 | 2.58 |
| Petal shape | Circular to obovate | Circular to obovate |
| Petal spacing overlapping | Overlapping | Separate to |
| Petal apex shape | Circular | Circular |
| Petal margin | Entire | Entire |
| Petal base shape | Obovate | Obovate |
| Petal length (cm) | 0.96 | 1.05 |
| Petal width (cm) | 1.05 | 0.99 |
| Petal length/width ratio | 0.92 | 1.07 |
| Petal count | 5.16 | 5.33 |
| Petal color | White Group 155D | White Group 155D |
| Stigma color | Yellow-Green Group 150B | Yellow-Green Group 153D |

TABLE 6-continued

| Characteristic | 'Keepsake' | 'Flavorfest' |
|---|---|---|
| Style color | Yellow-Green Group 150A | Yellow-Green Group 150B |
| Anther color | Yellow-Orange Group 20A | Yellow-Orange Group 18A |
| Anther count | 19.2 | 24.6 |
| Filament color | Yellow-Green Group 150B | Yellow-Green Group 154D |
| Blooming habit | Cyme | Cyme |
| Anther number | 19.2 | 24.6 |

Table 7 shows fruit characteristics of the new cultivar compared to 'Flavorfest'. These characteristics include number of berries per truss, fruiting truss attitude, fruit length, fruit diameter, fruit length/width ratio, fruit weight, relative fruit size, predominant fruit shape, difference in shape between primary and secondary fruit, band without achenes, evenness of fruit surface, top color, non-blush side color, blush side color, internal color, achene color, achene count per fruit, insertion of calyx, pose of calyx segments, size of calyx in relation to fruit, ease of calyx removal, firmness of flesh, evenness of flesh color, distribution of flesh color, sweetness, acidity, brix, pH, titratable acidity, texture when tasted, time of flowering, harvest maturity (50% of plants with ripe fruit), type of bearing, and yield.

TABLE 7

| Characteristic | 'Keepsake' | 'Flavorfest' |
|---|---|---|
| Number of berries per fruiting truss | 7.0 | 10.6 |
| Fruiting truss attitude | Prostrate | Prostrate |
| Diameter fruit (cm) | 4.6 | 4.3 |
| Length fruit (cm) | 4.0 | 3.6 |
| Ratio fruit length/width | 0.9 to 1.1 | 0.8 to 0.9 |
| Weight fruit (g) | 13.8 | 14.8 |
| Relative fruit size | Medium to large | Medium to large |
| Predominant fruit shape | Conic to oblate | Conic to oblate |
| Difference in shape between primary and secondary fruits | Moderate | Significant; depressed oblate primary fruits |
| Band without achenes | Narrow | Absent to narrow |
| Evenness of fruit surface | Very even | Even |
| Color of top of fruit | Red Group 45A | Red Group 46A |

TABLE 7-continued

| Characteristic | 'Keepsake' | 'Flavorfest' |
|---|---|---|
| Non-blush side color | Red Group 44A, 45A | Red Group 45A, 46A |
| Blush side color | Red Group 44A, 45A, 46A | Red Group 45A, 46A |
| Internal flesh color | Orange-Red Group 33A, White 155D | Orange-Red Group 33A, White 155D |
| Achenecolor | Yellow-Green Group 151B, Red Group 45A | Yellow-Green Group 153C, Red Group 46A |
| Achene count | 206 | 312 |
| Insertion of calyx | Slight | Slight, more depressed on primaries |
| Pose of calyx segments | Reflexed to spreading | Spreading to clasping |
| Size of calyx in relation to fruit | Larger | Slightly smaller |
| Ease of calyx removal | Difficult | Difficult |
| Firmness of flesh | Medium to firm | Medium to firm |
| Evenness of flesh color | Not even | Not even |
| Distribution of flesh color | Orange-red heart, white ring, orange red exterior | Orange-red heart, white ring, orange red exterior |
| Sweetness | Very sweet | Sweet |
| Acidity | Medium to mild | Medium |
| Brix (percent soluble solids) | 9.0 | 8.0 |
| pH | 3.8 | 3.8 |
| Texture when tasted | Fine and juicy | Fine and juicy |
| Time of flowering | April to May | April to May |
| Harvest maturity (50% of plant with ripe fruit) | Late May to early June | Late May to early June |
| Type of bearing | Short Day/June Bearing | Short Day/June Bearing |
| Yield (kg/plant) | 0.57 | 0.90 |

COMPARISON WITH PARENTAL CULTIVARS

When 'Keepsake' is compared to female parent, B1031 (unpatented), a full sibling of 'Flavorfest' (unpatented), the fruits are more uniform in shape. When 'Keepsake' is compared to male parent, B1181 (unpatented), the plants are more resistant to foliar diseases.

We claim:

1. A new and distinct cultivar of strawberry plant, substantially as illustrated and described herein.

* * * * *